US010857053B2

(12) United States Patent
Yano et al.

(10) Patent No.: US 10,857,053 B2
(45) Date of Patent: Dec. 8, 2020

(54) ROBOTIC OPERATING TABLE AND ROBOTIC OPERATING TABLE OPERATION APPARATUS

(71) Applicants: MEDICAROID CORPORATION, Kobe (JP); KAWASAKI JUKOGYO KABUSHIKI KAISHA, Kobe (JP)

(72) Inventors: Yutaro Yano, Kobe (JP); Yoshiyuki Tamura, Kobe (JP); Yukihiko Kitano, Kobe (JP); Mitsuichi Hiratsuka, Kobe (JP); Hiroaki Kitatsuji, Kobe (JP)

(73) Assignees: MEDICAROID CORPORATION, Kobe (JP); KAWASAKI JUKOGYO KABUSHIKI KAISHA, Kobe (JP)

( * ) Notice: Subject to any disclaimer, the term of this patent is extended or adjusted under 35 U.S.C. 154(b) by 356 days.

(21) Appl. No.: 15/906,708

(22) Filed: Feb. 27, 2018

(65) Prior Publication Data

US 2018/0243151 A1    Aug. 30, 2018

(30) Foreign Application Priority Data

Feb. 28, 2017    (JP) .................................. 2017-035693

(51) Int. Cl.
*A61G 13/04*    (2006.01)
*A61G 13/06*    (2006.01)
*A61B 5/00*    (2006.01)

(52) U.S. Cl.
CPC .............. *A61G 13/04* (2013.01); *A61B 5/704* (2013.01); *A61G 13/06* (2013.01); *A61B 5/7475* (2013.01);

(Continued)

(58) Field of Classification Search
CPC ........ A61G 13/00; A61G 13/02; A61G 13/04; A61G 13/0407; A61G 13/06; A61G 13/08;

(Continued)

(56) References Cited

U.S. PATENT DOCUMENTS 7,669,261 B2    3/2010 Fruh et al.
7,860,550 B2    12/2010 Saracen et al.
(Continued)

FOREIGN PATENT DOCUMENTS

EP    1028684 B1    3/2004
JP    2014-100301 A    6/2014
JP    2016-054860 A    4/2016

*Primary Examiner* — Dale Moyer
(74) *Attorney, Agent, or Firm* — Metrolex IP Law Group, PLLC

(57) ABSTRACT

A robotic operating table may include: a table on which to place a patient; and a robotic arm including a plurality of joints, and having a first end supported on a base fixed to a floor, and a second end supporting the table; and an operation device including: a mode-set operation receiving unit that receives a set operation to set a rotation mode for rotating the table; a move operation receiving unit that receives a move operation to move the table; and a display. When the mode-set operation receiving unit receives the set operation to set the rotation mode, the display may display setting information for setting a rotation center position of the table. When the move operation receiving unit receives the move operation in a state where the rotation center position is set, the robotic arm may rotate the table about a rotation axis at the rotation center position.

20 Claims, 9 Drawing Sheets

(52) U.S. Cl.
CPC ...... *A61B 2505/05* (2013.01); *A61G 2203/14* (2013.01); *A61G 2203/16* (2013.01); *A61G 2203/20* (2013.01); *A61G 2210/50* (2013.01)

(58) Field of Classification Search
CPC ...... A61G 13/10; A61G 13/101; A61G 7/018; A61G 7/1017; A61G 7/1046; A61G 13/0018; A61G 13/1295; A61B 5/704; A61B 6/04; A61B 6/0407; A61B 90/50; A61B 2034/742; A61B 1/00045; A61B 6/0442; A61B 5/0555; A61B 6/0457
See application file for complete search history.

(56) References Cited

U.S. PATENT DOCUMENTS

| | | | |
|---|---|---|---|
| 8,126,114 B2 | 2/2012 | Naylor et al. | |
| 8,160,205 B2 | 4/2012 | Saracen et al. | |
| 9,326,907 B2 | 5/2016 | Marie | |
| 2005/0228255 A1* | 10/2005 | Saracen | A61B 6/0457 600/407 |
| 2005/0234327 A1* | 10/2005 | Saracen | A61B 6/4458 600/407 |
| 2015/0000038 A1 | 1/2015 | Obi | |
| 2018/0085603 A1* | 3/2018 | Kruesi | A61N 5/1081 |
| 2018/0160994 A1* | 6/2018 | Harrington | A61N 5/1082 |
| 2019/0167212 A1* | 6/2019 | Pinault | A61N 5/1049 |

* cited by examiner

ROBOTIC OPERATING TABLE AND ROBOTIC OPERATING TABLE OPERATION APPARATUS

CROSS REFERENCE TO RELATED APPLICATIONS

This application claims priority from prior Japanese Patent Application No. 2017-035693 filed with the Japan Patent Office on Feb. 28, 2017, entitled "ROBOTIC OPERATING TABLE AND ROBOTIC OPERATING TABLE OPERATION APPARATUS", the entire contents of which are incorporated herein by reference.

BACKGROUND

The disclosure relates to a robotic operating table, a hybrid operation room system, and a robotic operating table operation apparatus.

Japanese Patent Application Publication No. 2014-100301 discloses a hybrid operation room system including a combination of a radiographic fluoroscopic imaging apparatus and an operating table. In Japanese Patent Application Publication No. 2014-100301, the operating table includes a movable top panel on which to place a subject (patient) and a base supporting the movable top panel. The movable top panel of the operating table is slidable in parallel to horizontal directions along the base, which is fixed to the floor. Also, the base of the operating table is freely extendable and contractible in the vertical direction and capable of raising and lowering the movable top panel in the vertical direction.

SUMMARY

Problems with an operating table as described in Japanese Patent Application Publication No. 2014-100301 are that the range of horizontal movement of the movable top panel is small and the freedom of movement of the movable top panel is poor as well. Thus, with such an operating table, it is difficult to move the movable top panel to various positions (patient receiving position, anesthetization position, surgical operation position, imaging position, and so on) desired by medical persons such as surgeons, assistants, nurses, and medical technicians, and it is also difficult to leave sufficient space around the positions at which the medical persons stand due to the small range of movement of the movable top panel. These make it difficult to perform surgery smoothly.

For this reason, there has been a demand from medical persons for an operating table in which a top panel with a patient placed thereon can be moved in a larger range than in the operating table described above. Further, there has also been a demand for providing an operating table capable of changing the rotation center position of a top panel (table) in a case of rotating the top panel.

One or more embodiments may provide a robotic operating table and a hybrid operation room system capable of achieving a large range and freedom of movement of a table on which to place a patient and also changing the rotation center position of the table, and also provides a robotic operating table operation apparatus capable of changing the rotation center position of a table.

A robotic operating table according to one or more embodiments may include: a table on which to place a patient; and a robotic arm including a plurality of joints, and having a first end supported on a base fixed to a floor, and a second end supporting the table; and an operation device including: a mode-set operation receiving unit that receives a set operation to set a rotation mode for rotating the table; a move operation receiving unit that receives a move operation to move the table; and a display. When the mode-set operation receiving unit receives the set operation to set the rotation mode, the display may display setting information for setting a rotation center position of the table. When the move operation receiving unit receives the move operation in a state where the rotation center position is set based on the setting information, the robotic arm may rotate the table about a rotation axis at the rotation center position.

A robotic operating table according to one or more embodiments may include: a table on which to place a patient; a robotic arm including a plurality of joints, and having a first end supported on a base fixed to a floor, and a second end supporting the table; and an operation device including: a mode-set operation receiving unit that receives a set operation to set a rotation mode for rotating the table; a move operation receiving unit that receives a move operation to move the table; and a display. When the mode-set operation receiving unit receives the set operation to set the rotation mode, the display may display setting information for setting a rotation axis position of the table. When the move operation receiving unit receives the move operation in a state where the rotation axis position is set based on the setting information, the robotic arm may rotate the table about a rotation axis at the set rotation axis position.

An operation device with which a user operates a robotic operating table according to one or more embodiments may include a table on which to place a patient. The operation device may include: a mode-set operation receiving unit that receives a set operation to set a rotation mode for rotating the table; a move operation receiving unit that receives a move operation to move the table; and a display. The robotic operating table may include: the table; and a robotic arm including a plurality of joints, and having a first end supported on a base fixed to a floor, and a second end supporting the table. When the mode-set operation receiving unit receives the set operation to set the rotation mode, the display may display setting information for setting a rotation center position of the table.

A hybrid operation system according to one or more embodiments may include: a robotic operating table; and at least one of a radiographic imaging apparatus configured to capture a radiographic projection image of a patient and a magnetic resonance imaging apparatus configured to capture a magnetic resonance image of a patient. The robotic operating table may include: a table on which to place a patient; a robotic arm including a plurality of joints, and having a first end supported on a base fixed to a floor, and a second end supporting the table; and an operation device including a mode-set operation receiving unit that receives a set operation to set a rotation mode for rotating the table, a move operation receiving unit that receives a move operation to move the table, and a display. When the mode-set operation receiving unit receives the set operation to set the rotation mode, the display may display setting information for setting a rotation center position of the table. When the move operation receiving unit receives the move operation in a state where the rotation center position is set based on the setting information, the robotic arm may rotate the table about a rotation axis at the rotation center position.

DETAILED DESCRIPTION

Embodiments are explained below with reference to the drawings.

First Embodiment (Configuration of Robotic Operating Table)

The configuration of a robotic operating table 100 according to this embodiment is explained with reference to FIG. 1 to FIG. 14.

Figure 1:
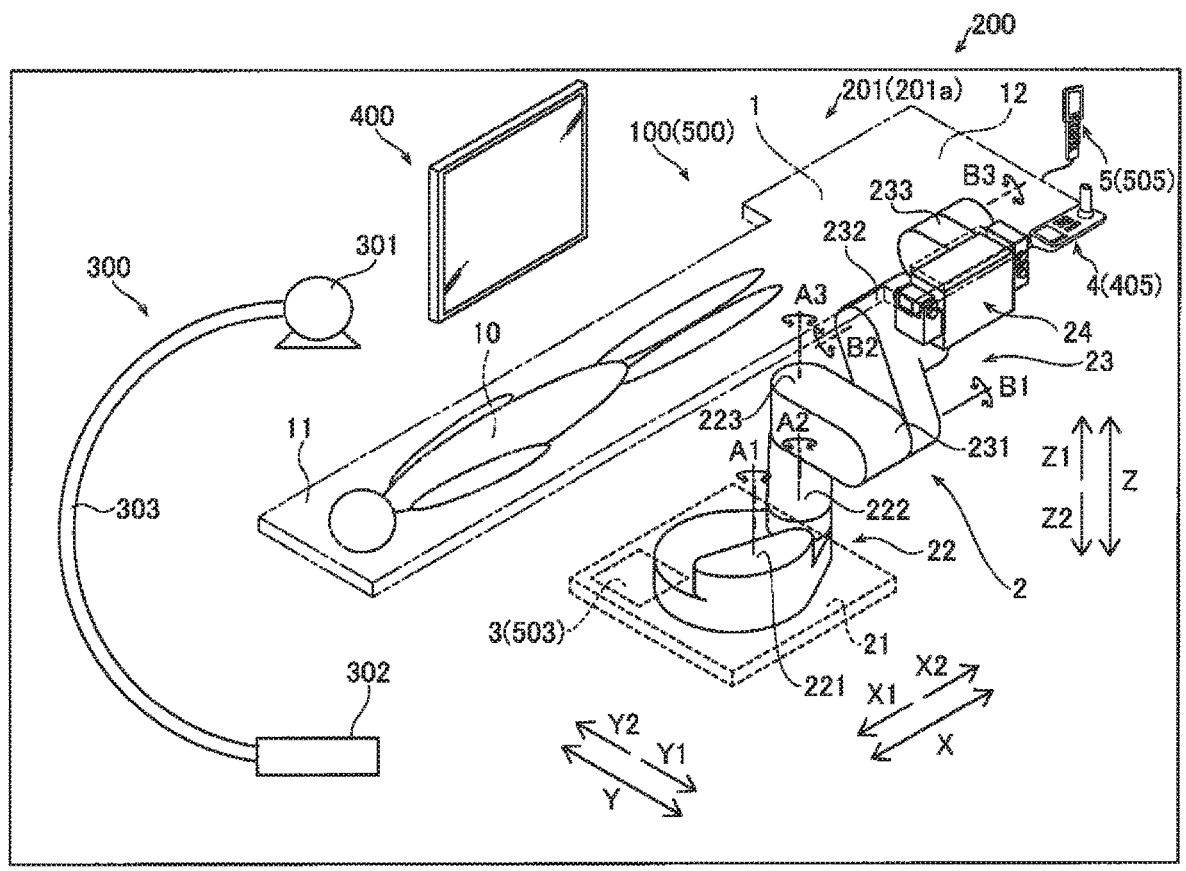
FIG. 1 is a view illustrating an overview of operating rooms including robotic operating tables according to first and second embodiments.

As illustrated in FIG. 1, the robotic operating table 100 is provided in an operating room 200. A radiographic imaging apparatus 300 that captures a radiographic projection image of a patient 10 is provided in the operating room 200. The operating room 200 is a hybrid operating room. In other words, a hybrid operation room system 201 including the robotic operating table 100 and the radiographic imaging apparatus 300 is provided in the operating room 200. Also, a display 400 that displays information on surgery is provided in the operating room 200. The display 400 is suspended from an arm (not illustrated), for example, and is movable inside the operating room 200.

The robotic operating table 100 is used as an operating table for operations performed in a setting such as a surgery or internal medicine setting. The robotic operating table 100 is capable of moving a table 1 to a placement position for placing the patient 10 onto the table 1. Also, the robotic operating table 100 is capable of moving the patient 10 to a patient receiving position, an anesthetization position, a surgical operation position, an examination position, a treatment position, a radiographic imaging position, a patient passing position, and so on by moving the table 1 while the patient 10 is placed on the table 1. Also, the robotic operating table 100 is capable of tilting the patient 10 by tilting the table 1 while the patient 10 is placed on the table 1.

The robotic operating table 100 includes the table 1, on which to place the patient 10, an articulated robotic arm 2 (hereinafter, the robotic arm 2), a controller 3, an operation device 4, and an operation device 5.

Figure 2:
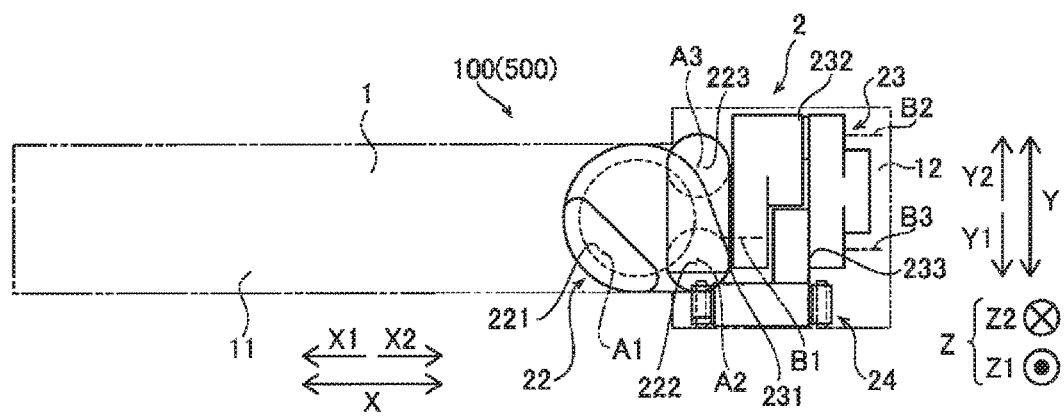
FIG. 2 is a plan view illustrating robotic operating tables according to first and second embodiments.

As illustrated in FIG. 1 and FIG. 2, the table 1 is formed in the shape of a substantially rectangular flat plate. Also, the upper surface of the table 1 is formed to be substantially flat. Note that, while the table 1 is rotatable about an axis extending in the vertical direction (Z direction), the horizontal direction along the longitudinal direction of the table 1 is defined as the X direction and the horizontal direction along the transverse direction of the table 1 is defined as the Y direction in one or more embodiments. In other words, the X direction and the Y direction represent directions based on the table 10.

The table 1 includes a radiolucent part 11 and a support part 12 supporting the radiolucent part 11.

The patient 10 is placed on the radiolucent part 11 of the table 1. The radiolucent part 11 is disposed on the X1 direction side of the table 1. The radiolucent part 11 is formed in a substantially rectangular shape. The radiolucent part 11 is made of a radiolucent material. The radiolucent part 11 is made of a carbon material (graphite), for example. The radiolucent part 11 is made of a carbon fiber reinforced plastic (CFRP), for example. In this way, an image of the patient 10 can be captured using X rays while the patient 10 is placed on the radiolucent part 11.

The support part 12 of the table 1 is connected to the robotic arm 2. The support part 12 is disposed on the X2 direction side of the table 1. The support part 12 is formed in a substantially rectangular shape. The support part 12 supports the radiolucent part 11. The support part 12 is made of a material smaller in radiolucency than the material the radiolucent part 11 is made of. The support part 12 is made of metal, for example. The support part 12 is made of a steel material or an aluminum material, for example.

The table 1 is moved by the robotic arm 2. Specifically, the table 1 is movable in the X direction, which is a horizontal direction, in the Y direction, which is a horizontal direction perpendicular to the X direction, and in the Z direction, which is perpendicular to the X direction and the Y direction and is the vertical direction. Moreover, the table 1 is rotatable (capable of being caused to roll) about an axis extending in the X direction. The table 1 is also rotatable (capable of being caused to pitch) about an axis extending in the Y direction. The table 1 is also rotatable (capable of being caused to yaw) about an axis extending in the Z direction.

The robotic arm 2 moves the table 1. One end of the robotic arm 2 is supported on a base 21 fixed to the floor, while the opposite end supports the table 1. Specifically, the one end of the robotic arm 2 is supported on the base 21 to be rotatable about a base rotation axis (rotation axis A1) extending in the vertical direction (Z direction). The base 21 is a base buried in and fixed to the floor. The base 21 is provided substantially at the center of the range of movement of the table 1 in a plan view (as seen from the Z direction). Also, the opposite end of the robotic arm 2 supports the table 1 at a position near its one end in the longitudinal direction of the table 1 (X direction). Specifically, the opposite end of the robotic arm 2 supports the support part 12, which is disposed on the one end side of the table 1 in the longitudinal direction of the table 1.

The robotic arm 2 is capable of being disposed in such a posture as to be entirely hidden under the table 1 (Z2 direction side) in a plan view (as seen from the Z1 direction). For example, the robotic arm 2 is housed in a housing space which is a space under the table 1 when the table 1 is positioned at the surgical operation position. Specifically, the robotic arm 2 is capable of being disposed in such a posture as to be folded and completely hidden under the table 1 in the plan view (as seen from the Z1 direction) in a state where the robotic arm 2 has moved the table 1 to a position for performing a surgical operation or treatment on the patient 10 placed on the table 1. Meanwhile, the length of the robotic arm 2 in the folded posture in the direction parallel to the longitudinal direction of the table 1 is equal to or shorter than ½ of the length of the table 1 in the longitudinal direction of the table 1.

The robotic arm 2 includes a horizontal articulated assembly 22, a vertical articulated assembly 23, and a pitch mechanism 24. The horizontal articulated assembly 22 includes horizontal joints 221, 222, and 223. The vertical articulated assembly 23 includes vertical joints 231, 232, and 233. Note that the horizontal joints 221 to 223 and the vertical joints 231 to 233 are an example of the "joints" in one or more recited embodiments.

The robotic arm 2 is capable of moving the table 1 with seven degrees of freedom. Specifically, with the horizontal articulated assembly 22, the robotic arm 2 has three degrees of freedom to rotate about the rotation axis A1, extending in the vertical direction, rotate about a rotation axis A2 extending in the vertical direction, and rotate about a rotation axis A3 extending in the vertical direction. Further, with the vertical articulated assembly 23, the robotic arm 2 has three degrees of freedom to rotate about a rotation axis B1 extending a horizontal direction, rotate about a rotation axis B2 extending in the horizontal direction, and rotate about a rotation axis B3 extending in the horizontal direction. Furthermore, with the pitch mechanism 24, the robotic arm 2 has one degree of freedom to allow the table 1 to pitch about a rotation axis extending in the transverse direction of the table 1 (Y direction).

Figure 3:
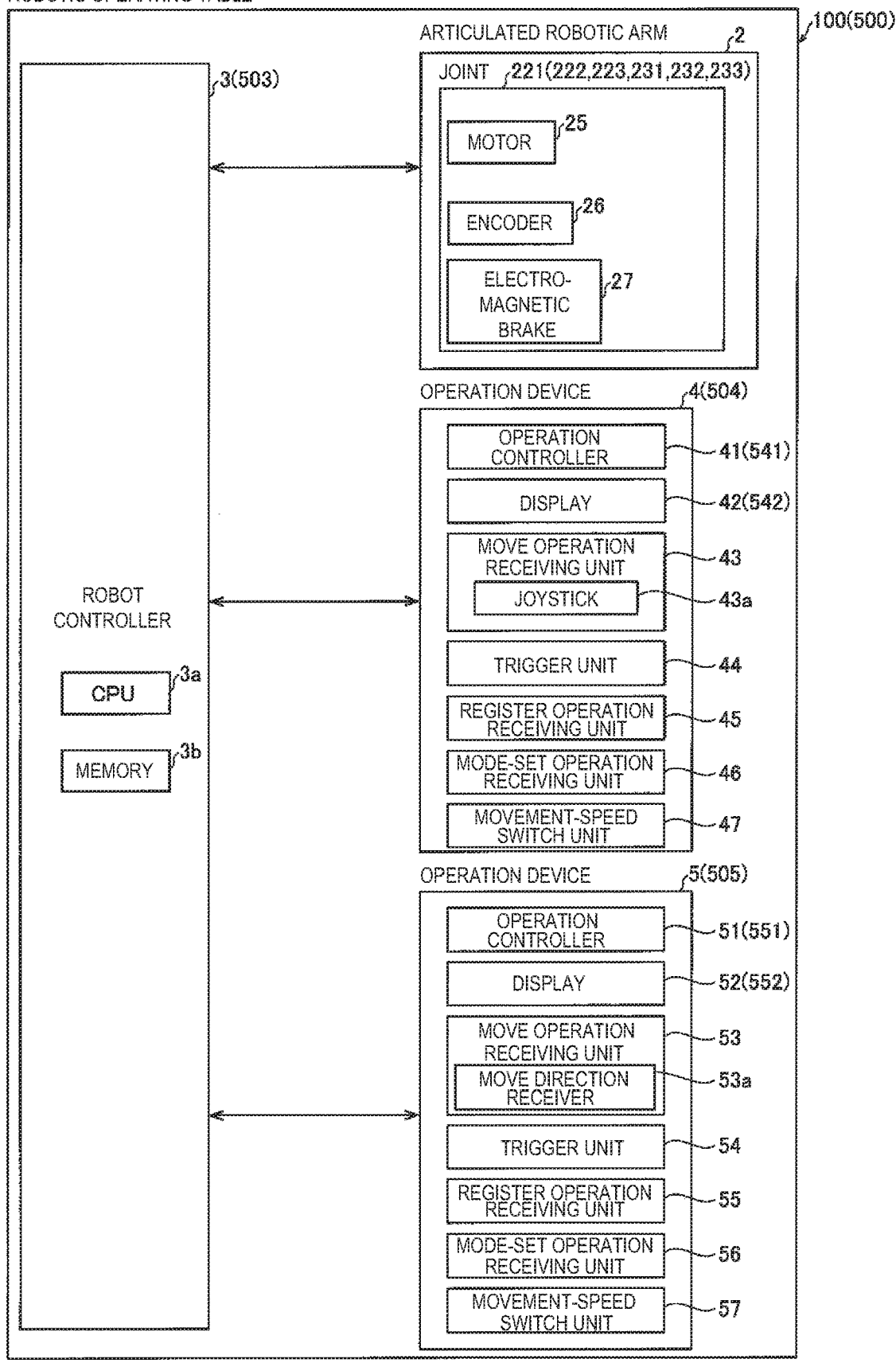
FIG. 3 is a block diagram illustrating control configurations of robotic operating tables according to first and second embodiments.

As illustrated in FIG. 3, the joints of the robotic arm 2 (horizontal joints 221 to 223 and vertical joints 231 to 233) each include a motor 25, an encoder 26, an electromagnetic brake 27, and a reducer (not illustrated). The motor 25 is a drive source for the joint to rotate the table 10. The motor 25 includes a servomotor. Also, the motor 25 is driven based on control by the controller 3. The encoder 26 measures the amount of rotation of the motor 25. Also, the encoder 26 transmits the result of the measurement of the amount of rotation of the motor 25 to the controller 3. The controller 3 acquires position information on the table 1, posture information on the table 1, and posture information on the robotic arm 2 based on the result of the measurement by the encoder 26. The electromagnetic brake 27 is a negative actuated-type electromagnetic brake that stops the rotation by the motor 25. Specifically, the electromagnetic brake 27 cancels braking of the motor 25 when the motor 25 is energized, and brakes the motor 25 when the motor 25 is de-energized. The electromagnetic brake 27 may be an electromagnetic brake incorporated in the motor 25 or an electromagnetic brake externally mounted to the motor 25.

Also, the robotic arm 2 causes the table 1 to yaw about an axis extending in the vertical direction (Z direction) by using at least one of the horizontal joints (at least one of 221, 222, and 223). Further, the robotic arm 2 causes the table 1 to roll about an axis extending in the longitudinal direction (X direction) by using at least one of the vertical joints (at least one of 231, 232, and 233). Furthermore, the robotic arm 2 causes the table 1 to pitch about an axis extending in the transverse direction (Y direction) by using the pitch mechanism 24.

The controller 3 is control circuitry including, for example, a CPU (Central Processing Unit) $3a$ and a memory $3b$. The memory $3b$ according to one or more embodiments may include such devices as a flash memory device, magnetic disk device such as a hard disk drive, and an optical disk device that reads data from a recording medium. In one or more embodiments, for example, the recording medium may include Blu-ray disk, CD-ROM (Compact Disk Read Only Memory), DVD (Digital Versatile Disk). The controller 3 is disposed inside the base 21 and controls movement of the table 1 by the robotic arm 2. Specifically, the controller 3 moves the table 1 by controlling the motion of the robotic arm 2 based on an operation input by a medical person (user).

Figure 4:
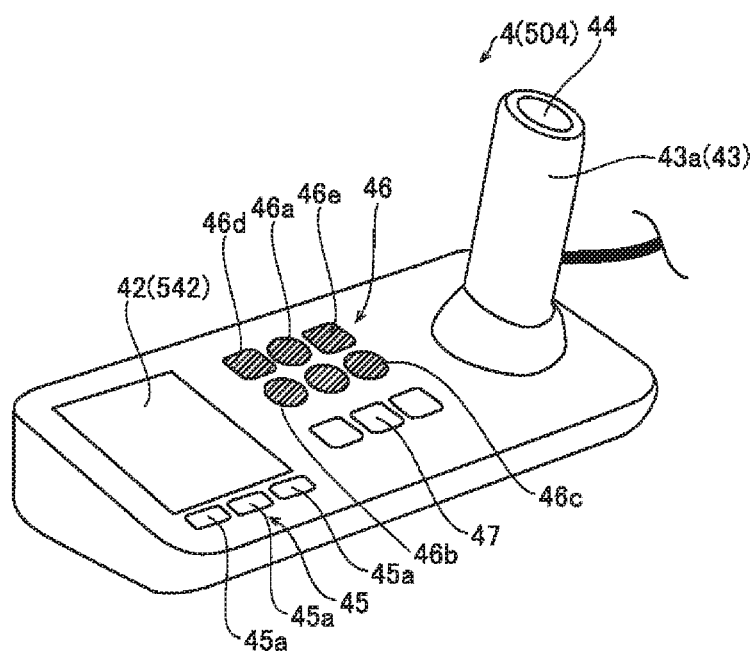
FIG. 4 is a perspective view illustrating an operation device with a joystick of robotic operating tables according to first and second embodiments.
Figure 5:
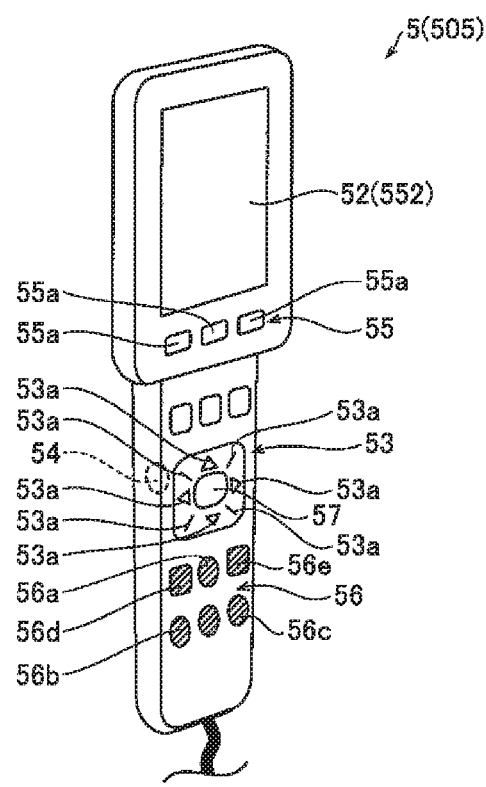
FIG. 5 is a perspective view illustrating an operation device with move direction receivers of robotic operating tables according to first and second embodiments.

As illustrated in FIG. 3 to FIG. 5, the operation device 4 and the operation device 5 receive operations input by a medical person (user) for moving the table 1. The operation devices 4 and 5 are each capable of receiving operations for the table 1. The operation device 4 is an operation device mainly used while mounted to the table 1. The operation device 5 is an operation device mainly used from a position away from the table 1. The operation devices 4 and 5 are detachably mounted to the table 1 by being engaged with engagement portions (not illustrated) provided on a side surface of the support part 12 of the table 1. The operation devices 4 and 5 are connected to the controller 3 so as to be capable of making wired communication with the controller 3.

As illustrated in FIG. 3 and FIG. 4, the operation device 4 includes an operation controller 41, a display 42, a move operation receiving unit 43, a trigger unit 44, a register operation receiving unit 45, a mode-set operation receiving unit 46, and a movement-speed switch unit 47. As illustrated in FIG. 3 and FIG. 5, the operation device 5 includes an operation controller 51, a display 52, a move operation receiving unit 53, a trigger unit 54, a register operation receiving unit 55, a mode-set operation receiving unit 56, and a movement-speed switch unit 57.

The operation controller 41 (51) controls units in the operation device 4 (5) based on operations input by a medical person (user). For example, the operation controller 41 (51) controls imagery to be displayed on the display 42 (52) based on an operation input by the medical person (user). Moreover, the operation controller 41 (51) transmits operation information indicating an operation input by the medical person (user) to the controller 3. The controller 3 performs control that causes the robotic arm 2 to move the table 1 based on the received operation information.

The display 42 (52) displays the state of the table 1, the state of operation on the operation device 4 (5), an operation screen, and so on. The display 42 (52) includes a display, such as liquid crystal display or an organic EL (Electro Luminescence) display. Meanwhile, in the operating room 200, the controller 3 of the robotic operating table 100, the operation controller 41 (51), and the display 400 (see FIG. 1) are communicatively connected to each other, and the display 400 is capable of displaying the state of the table 1, the state of operation on the operation device 4 (5), the operation screen, and so on. The display 400 is capable of displaying, for example, an image displayed on the display 42 (52) of the operation device 4 (5). In this way, multiple medical persons in the operating room 200 can check the state of operation on the robotic operating table 100 at the same time. Also, the display 400 can be a touchscreen-type input and display and may receive an operation input by a medical person (user) for moving the table 1 through an operation on a screen.

The move operation receiving unit 43 (53) receives a move operation to move the table 1 from a medical person (user). The move operation receiving unit 43 of the operation device 4 includes a joystick 43a. The joystick 43a is operated by being tilted. Moreover, the joystick 43a receives an operation for moving the table 1 that reflects the direction of the tilt and the angle of the tilt. The move operation receiving unit 53 of the operation device 5 includes multiple (eight) move direction receivers 53a provided respectively for directions in which to move the table 1. In other words, the move direction receivers 53a are provided for eight directions. Each of the move direction receivers 53a receives an operation for moving the table 1 by being pressed. Meanwhile, the eight move direction receivers 53a are capable of lighting up using incorporated light sources formed of light emitting diodes.

The trigger unit 44 (54) is provided to enable operations on the move operation receiving unit 43 (53). Specifically, the trigger unit 44 (54) has a function to allow energization of the motors 25 by being operated. The controller 3 performs control that energizes the motors 25 while the trigger unit 44 (54) is operated. Thus, operating the trigger unit 44 (54) cancels braking of the motors 25 by the electromagnetic brakes 27. Hence, operations on the move operation receiving unit 43 (53) are enabled and the table 1 can be moved only while the trigger unit 44 (54) is operated. On the other hand, in the robotic operating table 100, the motors 25 are de-energized when the operation on the trigger unit 44 (54) is canceled. The controller 3 actuates the electromagnetic brakes 27 by stopping the energization of the motors 25 when the trigger unit 44 (54) is not operated. Thus, cancelling the operation on the trigger unit 44 (54) causes the electromagnetic brakes 27 to brake the motors 25. Hence, any operations on the move operation receiving unit 43 (53) are disabled and the table 1 cannot be moved when the trigger unit 44 (54) is not operated.

The trigger unit 44 of the operation device 4 is provided at the tip of the joystick 43a. Pressing the trigger unit 44 of the operation device 4 enables operations on the joystick 43a. On the other hand, any operations on the joystick 43a are disabled in the state where the pressing of the trigger unit 44 is canceled. The trigger unit 54 of the operation device 5 is provided at the surface opposite from the surface where the move direction receivers 53a are provided. Pressing the trigger unit 54 of the operation device 5 enables operations on the move direction receivers 53a. On the other hand, any operations on the move direction receivers 53a are disabled in the state where the pressing of the trigger unit 54 is canceled.

The register operation receiving unit 45 (55) receives, from the user, a register operation and a set operation for a to-be-registered or registered position as the position a movement destination of the table 1. The register operation receiving unit 45 (55) includes multiple (three) register operation receiving buttons 45a (55a). The register operation receiving unit 45 (55) receives a register operation and a set operation for a to-be-registered or registered position with each register operation receiving button 45a (55a). In other words, the robotic operating table 100 is capable of registering multiple different to-be-registered positions. The register operation receiving unit 45 (55) receives a registration operation or a setting operation for a to-be-registered or registered position when a register operation receiving button 45a (55a) is pressed.

When the register operation receiving unit 45 (55) receives a register operation, the controller 3 stores the position of the table 1, the posture of the table 1, and the posture of the robotic arm 2 at the current position for registration into the memory 3b as a registered position. Also, when the register operation receiving unit 45 (55) receives a set operation, the controller 3 sets the corresponding registered position as the movement destination of the table 1. Then, when the move operation receiving unit 43 (53) receives a move operation with the registered position set as the movement destination of the table 1, the controller 3 controls the motion of the robotic arm 2 such that the table 1 will be placed at the registered position with the position of the table 1, the posture of the table 1, and the posture of the robotic arm 2 stored in the memory 3b.

Figure 6:
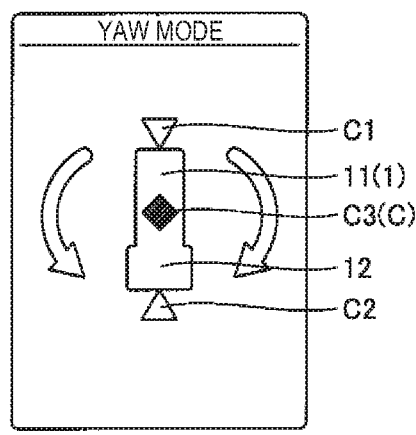
FIG. 6 is a diagram illustrating a yaw mode of a robotic operating table according to a first embodiment.
Figure 7:
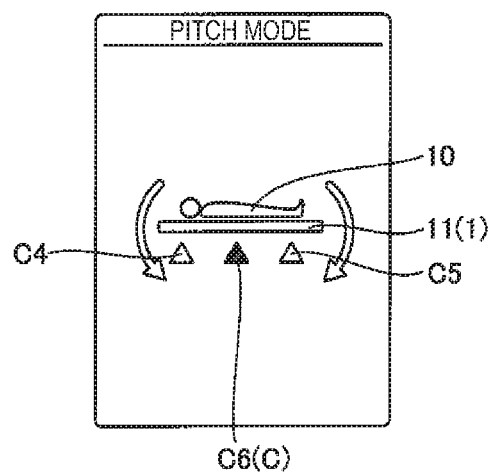
FIG. 7 is a diagram illustrating a pitch mode of a robotic operating table according to a first embodiment.
Figure 8:
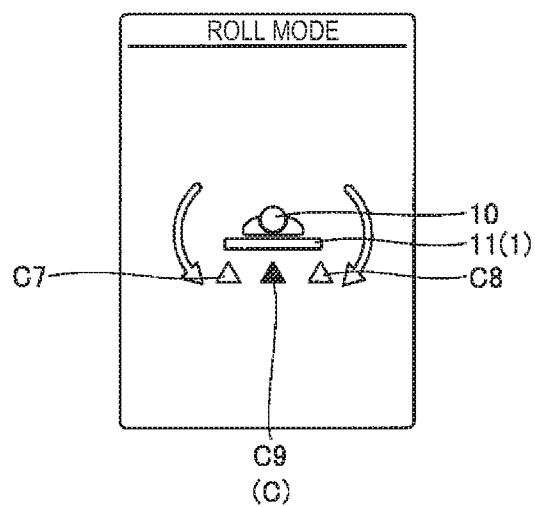
FIG. 8 is a diagram illustrating a roll mode of a robotic operating table according to a first embodiment.
Figure 9:
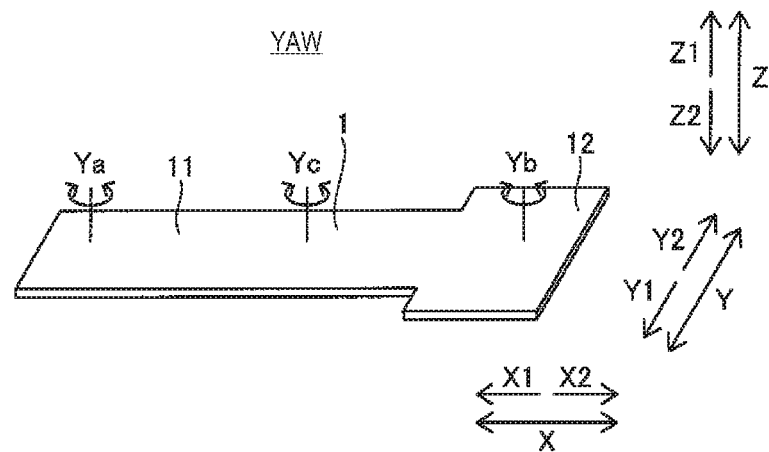
FIG. 9 is a diagram illustrating rotation of a table in a yaw mode of a robotic operating table according to a first embodiment.
Figure 10:
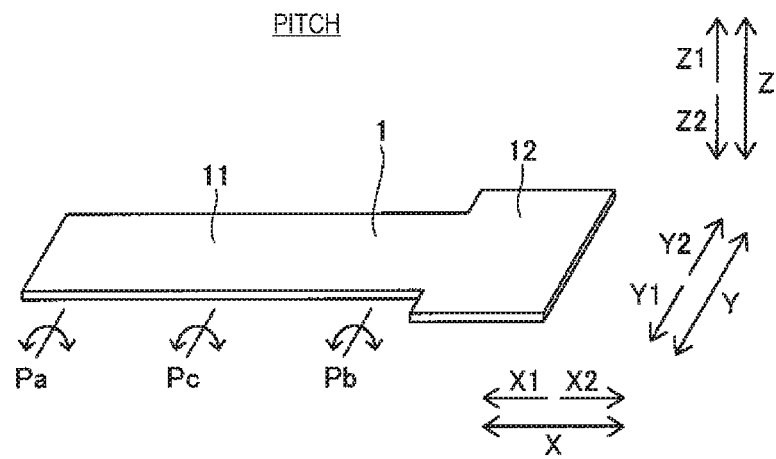
FIG. 10 is a diagram illustrating rotation of a table in a pitch mode of a robotic operating table according to a first embodiment.
Figure 11:
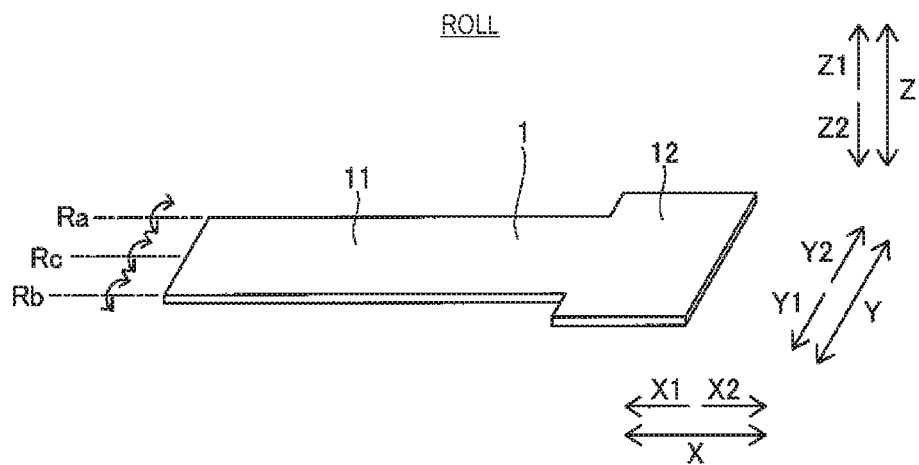
FIG. 11 is a diagram illustrating rotation of a table in a roll mode of a robotic operating table according to a first embodiment.

The mode-set operation receiving unit 46 (56) receives a set operation to set a rotation mode for rotating the table 1 about a rotation axis from the user. As illustrated in FIG. 6 to FIG. 8, the rotation mode includes: a yaw mode in which the table 1 is rotated in a horizontal plane about an axis extending in the vertical direction (Z direction); a pitch mode in which the table 1 is rotated about an axis extending in parallel to the transverse direction of the table 1 (Y direction); and a roll mode in which the table 1 is rotated about an axis extending in parallel to the longitudinal direction of the table 1 (X direction). In the yaw mode, the table 1 is caused to yaw based on an operation input by a medical person (user). In the pitch mode, the table 1 is caused to pitch based on an operation input by a medical person (user). In the roll mode, the table 1 is caused to roll based on an operation input by a medical person (user). Note that FIG. 6 to FIG. 8 respectively illustrate images displayed on the display 42 (52) and the display 400 when the above modes are set. The mode-set operation receiving unit 46 (56) includes yaw-mode receiving button 46a (56a) that receives a set operation to set the yaw mode, a pitch-mode receiving button 46b (56b) that receives a set operation to set the pitch mode, and a roll-mode receiving button 46c (56c) that receives a set operation to set the roll mode.

Here, in a first embodiment, when the mode-set operation receiving unit 46 (56) receives a set operation to set the rotation mode, the operation controller 41 (51) performs control that displays information for setting a rotation center position C to one of predefined positions on the display 42 (52) of the operation device 4 (5) and the display 400. Then, when the move operation receiving unit 43 (53) receives a move operation with the rotation center position C set, the controller 3 controls the motion of the robotic arm 2 to rotate the table 1 about the set rotation center position C.

Specifically, when the mode-set operation receiving unit 46 (56) receives a set operation to set the rotation mode, the operation controller 41 (51) performs control that displays graphic information (illustration) representing the table 1, graphic information (illustration) representing the patient 10, and graphic information (illustration) representing predefined positions on the display 42 (52) and the display 400 in such a manner that the rotation center position C can be set to one of the predefined positions. Also, when the rotation center position C is set, the operation controller 41 (51) performs control that displays information indicating the mode name of the set rotation mode and the set rotation center position C on the display 42 (52) of the operation device 4 (5) and the display 400. Also, when the rotation center position C is set, the operation controller 41 (51) performs control that displays the set rotation center position C in a visually recognizable manner on the display 42 (52) of the operation device 4 (5) and the display 400. For example, the operation controller 41 (51) performs control that displays the one of the predefined positions which is set as the rotation center position C and the positions which are not set as the rotation center position C in mutually different colors on the display 42 (52) of the operation device 4 (5) and the display 400.

As illustrated in FIG. 6, in the yaw mode, which is set by means of the yaw-mode receiving button 46a (56a), three positions C1, C2, and C3 are predefined as positions that can be set as the rotation center position C. FIG. 6 illustrates an example where the position C3 is set as the rotation center position C. Pressing the yaw-mode receiving button 46a (56a) in this state switches the state such that the position C2 is set as the rotation center position C. Pressing the yaw-mode receiving button 46a (56a) again switches the state such that the position C1 is set as the rotation center position C. In other words, each time the yaw-mode receiving button 46a (56a) is pressed, the position set as the rotation center position C is switched. The position C1 is a position set to rotate the table 1 about an axis Ya (see FIG. 9) extending in the vertical direction near one end of the table 1 in the longitudinal direction (X direction). In other words, the position C1 is a position set to rotate the table 1 about the axis Ya, extending in the vertical direction, on the head side of the patient 10. The position C2 is a position set to rotate the table 1 about an axis Yb (see FIG. 9) extending in the vertical direction near the opposite end of the table 1 in the longitudinal direction. In other words, the position C2 is a position set to rotate the table 1 about the axis Yb, extending in the vertical direction, on the foot side of the patient 10. The position C3 is a position set to rotate the table 1 about an axis Yc (see FIG. 9) extending in the vertical direction near the center of the table 1 in the longitudinal direction between the position C1 and the position C2. In other words, the position C3 is a position set to rotate the table 1 about the axis Yc, extending in the vertical direction, near the torso of the patient 10. Note that when the yaw mode is set, the operation controller 51 enables operations on the two, left and right move direction receivers 53a among the eight move direction receivers 53a and disables operations on the other six move direction receivers 53a. Also, the operation controller 51 turns on the light sources of the two, left and right move direction receivers 53a, operations on which have been enabled, to notify the user that the two, left and right move direction receivers 53a can be operated.

As illustrated in FIG. 7, in the pitch mode, which is set by means of the pitch-mode receiving button 46b (56b), three positions C4, C5, and C6 are predefined as positions that can be set as the rotation center position C. FIG. 7 illustrates an example where the position C6 is set as the rotation center position C. Pressing the pitch-mode receiving button 46b (56b) in this state switches the state such that the position C4 is set as the rotation center position C. Pressing the pitch-mode receiving button 46b (56b) again switches the state such that the position C5 is set as the rotation center position C. In other words, each time the pitch-mode receiving button 46b (56b) is pressed, the position set as the rotation center position C is switched. The position C4 is a position set to rotate the table 1 about an axis Pa (see FIG. 10) extending in the transverse direction (Y direction) near one end of the radiolucent part 11 of the table 1 in the longitudinal direction (X direction). In other words, the position C4 is a position set to rotate the table 1 about the axis Pa, extending in the transverse direction, on the head side of the patient 10. The position C5 is a position set to rotate the table 1 about an axis Pb (see FIG. 10) extending in the transverse direction near the opposite end of the radiolucent part 11 of the table 1 in the longitudinal direction. In other words, the position C5 is a position set to rotate the table 1 about the axis Pb, extending in the transverse direction, on the foot side of the patient 10. The position C6 is a position set to rotate the table 1 about an axis Pc (see FIG. 10) extending in the transverse direction near the center of the radiolucent part 11 of the table 1 in the longitudinal direction between the position C4 and the position C5. In other words, the position C6 is a position set to rotate the table 1 about the axis Pc, extending in the transverse direction, near the torso of the patient 10. Note that when the pitch mode is set, the operation controller 51 enables operations on the two, left and right move direction receivers 53a among the eight move direction receivers 53a and disables operations on the other six move direction receivers 53a. Also, the operation controller 51 turns on the light sources of the two, left and right move direction receivers 53a, operations on which have been enabled, to notify the user that the two, left and right move direction receivers 53a can be operated.

As illustrated in FIG. 8, in the roll mode, which is set by means of the roll-mode receiving button 46c (56c), three positions C7, C8, and C9 are predefined as positions that can be set as the rotation center position C. FIG. 8 illustrates an example where the position C9 is set as the rotation center position C. Pressing the roll-mode receiving button 46c (56c) in this state switches the state such that the position C7 is set as the rotation center position C. Pressing the roll-mode receiving button 46c (56c) again switches the state such that the position C8 is set as the rotation center position C. In other words, each time the roll-mode receiving button 46c (56c) is pressed, the position set as the rotation center position C is switched. The position C7 is a position set to rotate the table 1 about an axis Ra (see FIG. 11) extending in the longitudinal direction near one end of the radiolucent part 11 of the table 1 in the transverse direction (Y direction). In other words, the position C7 is a position set to rotate the table 1 about the axis Ra, extending in the longitudinal direction, on the left-hand side of the patient 10 in the left-right direction. The position C8 is a position set to rotate the table 1 about an axis Rb (see FIG. 11) extending in the longitudinal direction near the opposite end of the radiolucent part 11 of the table 1 in the transverse direction. In other words, the position C8 is a position set to rotate the table 1 about the axis Rb, extending in the longitudinal direction, on the right-hand side of the patient 10 in the left-right direction. The position C9 is a position set to rotate the table 1 about an axis Rc (see FIG. 11) extending in the longitudinal direction near the center of the radiolucent part 11 of the table 1 in the transverse direction between the position C7 and the position C8. In other words, the position C9 is a position set to rotate the table 1 about the axis Rc, extending in the longitudinal direction, near the center of the patient 10 in the left-right direction. Note that when the roll mode is set, the operation controller 51 enables operations on the two, left and right move direction receivers 53*a* among the eight move direction receivers 53*a* of the move operation receiving unit 53 and disables operations on the other six move direction receivers 53*a*. Also, the operation controller 51 turns on the light sources of the two, left and right move direction receivers 53*a*, operations on which have been enabled, to notify the user that the two, left and right move direction receivers 53*a* can be operated.

Also, in the case where display 42 (52) of the operation device 4 (5) and the display 400 are configured as touch-screens, a set operation to set the rotation center position C can be issued by operating the screen of the display 42 (52) or the display 400.

Also, when the move operation receiving unit 43 (53) receives a move operation in a state where the direction of rotation about the rotation center position C is set, the controller 3 controls the motion of the robotic arm 2 such that the table 1 will be rotated about the set rotation center position C in the direction of rotation specified in the move operation.

Figure 12:
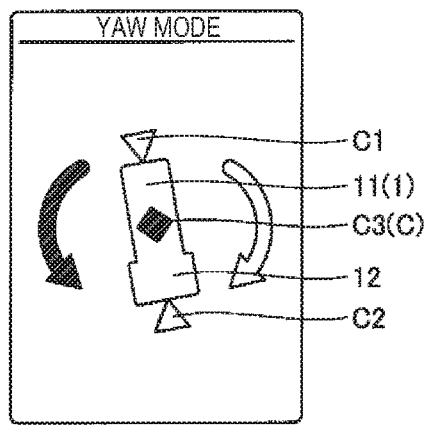
FIG. 12 is a diagram illustrating a yaw mode during rotation of a table of a robotic operating table according to a first embodiment.
Figure 13:
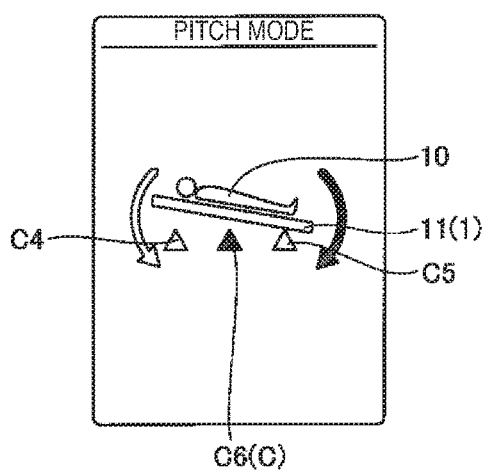
FIG. 13 is a diagram illustrating a pitch mode during rotation of a table of a robotic operating table according to a first embodiment.
Figure 14:
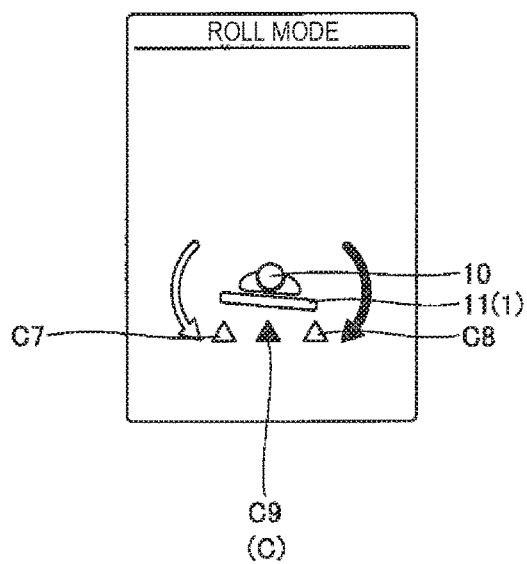
FIG. 14 is a diagram illustrating a roll mode during rotation of a table of a robotic operating table according to a first embodiment.

Also, as illustrated in FIG. 12 to FIG. 14, when the table 1 is rotated about the rotation center position C, the operation controller 41 (51) performs control that displays graphic information (illustration) indicating the rotational state of the table 1, graphic information (illustration) indicating the set rotation center position C, and graphic information (illustration) indicating the rotational direction of the table 1 on the display 42 (52) of the operation device 4 (5) and the display 400. In other words, when the table 1 is rotated about the rotation center position C, the operation controller 41 (51) performs control that displays each of the rotational state of the table 1, the rotation center position C, and the rotational direction in a visually recognizable manner on the display 42 (52) of the operation device 4 (5) and the display 400. For example, the operation controller 41 (51) performs control that displays the rotational direction of the table 1 that is being moved and the opposite rotational direction in mutually different colors on the display 42 (52) of the operation device 4 (5) and the display 400. Note that FIG. 12 to FIG. 14 respectively illustrates images displayed on the display 42 (52) and the display 400 when the above modes are set. Meanwhile, FIG. 12 illustrates an example where the table 1 is moved in a counterclockwise rotational direction, and FIG. 13 and FIG. 14 illustrate examples where the table 1 is moved in a clockwise rotational direction.

Also, in a first embodiment, the controller 3 performs control that causes the robotic arm 2 to move the table 1 while the move operation receiving unit 43 (53) is receiving a move operation.

Specifically, if the operation device 4 is receiving an operation input by a medical person (user), the controller 3 controls the motion of the robotic arm 2 to rotate the table 1 about the set rotation center position C while the joystick 43*a* is operated in a state where the mode-set operation receiving unit 46 (56) has received a set operation to set the rotation mode and the rotation mode has been set. In other words, if the operation device 4 is receiving an operation input from a medical person (user), the table 1 is rotated about the set rotation center position C only while the joystick 43*a* is operated.

Also, if the operation device 5 is receiving an operation input by a medical person (user), the controller 3 controls the motion of the robotic arm 2 to rotate the table 1 about the set rotation center position C while one of the two, left and right move direction receivers 53*a*, operations on which have been enabled, is operated in a state where the mode-set operation receiving unit 46 (56) has received a set operation to set the rotation mode and the rotation mode has been set. In other words, if the operation device 5 is receiving an operation input from a medical person (user), the table 1 is rotated about the set rotation center position C only while a move direction receiver 53*a* is operated.

Also, if one of the operation devices 4 and 5 is receiving an operation input by a medical person (user), the controller 3 controls the motion of the robotic arm 2 to rotate the table 1 about the set rotation center position C while the trigger unit 44 (54) and the move operation receiving unit 43 (53) are simultaneously operated in a state where the mode-set operation receiving unit 46 (56) has received a set operation to set the rotation mode and the rotation mode has been set. In other words, if the operation device 4 is receiving an operation input by a medical person (user), the table 1 is rotated about the set rotation center position C only while an operation of pressing the trigger unit 44 and an operation of tilting the joystick 43*a* are performed simultaneously. Also, if the operation device 5 is receiving an operation input by a medical person (user), the table 1 is rotated about the set rotation center position C only while an operation of pressing the trigger unit 54 and an operation of pressing a move direction receiver 53*a* are performed simultaneously.

Also, the mode-set operation receiving unit 46 (56) receives a set operation to set a linear movement mode in which the table 1 is linearly moved, from the user. The linear movement mode includes a horizontal movement mode in which the table 1 is linearly moved in a horizontal plane, and an elevation mode in which the table 1 is raised and lowered. The mode-set operation receiving unit 46 (56) includes a horizontal-movement-mode receiving button 46*d* (56*d*) that receives a set operation to set the horizontal movement mode and an elevation-mode receiving button 46*e* (56*e*) that receives a set operation to set the elevation mode. In the horizontal movement mode, which is set by pressing the horizontal-movement-mode receiving button 46*d* (56*d*), the table 1 is horizontally linearly moved based on an operation input by a medical person (user). When the horizontal movement mode is set, the operation controller 51 enables operations on the eight move direction receivers 53*a*. Also, the operation controller 51 turns on the light sources of the eight move direction receivers 53*a* to notify the user that the eight move direction receivers 53*a* can be operated. In the elevation mode, which is set by pressing the elevation-mode receiving button 46*e* (56*e*), the table 1 is linearly moved in the vertical direction (Z direction) base on an operation input by a medical person (user). When the elevation mode is set, the operation controller 51 enables operations on the two top and bottom move direction receivers 53*a* among the eight move direction receivers 53*a* and disables operations on the other six move direction receivers 53*a*. Also, the operation controller 51 turns on the light sources of the two top and bottom move direction receivers 53*a*, operations on which have been enabled, to notify the user that the two, top and bottom move direction receivers 53*a* can be operated. In the robotic operating table 100, the table 1 is moved when the trigger unit 44 (54) and the move operation receiving unit 43 (53) are operated with the motion mode selected by means of the mode-set operation receiving unit 46 (56).

The movement-speed switch unit 47 (57) receives an operation to change the movement speed of the table 1 from the user. Also, the movement-speed switch unit 47 (57)

receives an operation for changing the movement speed of the table 1 by being pressed. The robotic operating table 100 changes the movement speed of the table 1 to a different level of movement speed each time the movement-speed switch unit 47 (57) is pressed. For example, the movement speed of the table 1 can be changed through three levels of movement speed.

(Configuration of Radiographic Imaging Apparatus)

The configuration of the radiographic imaging apparatus 300 is explained with reference to FIG. 1.

As illustrated in FIG. 1, the radiographic imaging apparatus 300 is capable of capturing a radiographic projection image of the patient 10 placed on the table 1 of the robotic operating table 100. The radiographic imaging apparatus 300 includes an X-ray irradiation part 301, an X-ray detection part 302, and a C-arm 303. The X-ray irradiation part 301 and the X-ray detection part 302 are supported on the C-arm 303. The X-ray irradiation part 301 and the X-ray detection part 302 are moved with movement of the C-arm 303, and are positioned to face each other from opposite sides of the patient 10 during imaging of the patient 10 using X rays. For example, one of the X-ray irradiation part 301 and the X-ray detection part 302 is positioned in a space above the table 1 while the other is positioned in a space under the table 1. Also, during imaging of the patient 10 using X rays, the C-arm 303, supporting the X-ray irradiation part 301 and the X-ray detection part 302, is partly positioned in the spaces above and under the table 1 as well.

The X-ray irradiation part 301 is disposed to face the X-ray detection part 302. Also, the X-ray irradiation part 301 is capable of emitting X rays toward the X-ray detection part 302. The X-ray detection part 302 detects the X rays emitted by the X-ray irradiation part 301. The X-ray detection part 302 includes an FPD (Flat Panel Detector). The X-ray detection part 302 converts the detected X rays into electric signals and transmits them to an image processing unit (not illustrated).

The X-ray irradiation part 301 is connected to one end of the C-arm 303, and the X-ray detection part 302 is connected to the opposite end of the C-arm 303. The C-arm 303 has a substantially C-shape. In this way, the C-arm 303 can support the X-ray irradiation part 301 and the X-ray detection part 302 in such a position that the table 1 and the patient 10 are situated therebetween, during imaging of the patient 10 using X rays. The C-arm 303 is capable of moving relative to the table 1. Specifically, the C-arm 303 is capable of moving horizontally and vertically and also rotating about a horizontal rotation axis and a vertical rotation axis. In this way, the X-ray irradiation part 301 and the X-ray detection part 302 can be placed at a desired position relative to the patient 10 placed on the table 1. The C-arm 303 is moved by a drive part (not illustrated) based on an operation input by a medical person (user). The C-arm 303 is also manually movable by a medical person (user). Meanwhile, the radiographic imaging apparatus 300 and the display 400 are communicatively connected to each other. The display 400 is capable of displaying radiographic fluoroscopic images captured by the radiographic imaging apparatus 300 and a radiographic image captured by the radiographic imaging apparatus 300.

(Rotation-Center-Position Setting Process)

Next, a rotation-center-position setting process by the robotic operating table 100 in this embodiment is explained with reference to a flowchart in FIG. 15.

Figure 15:
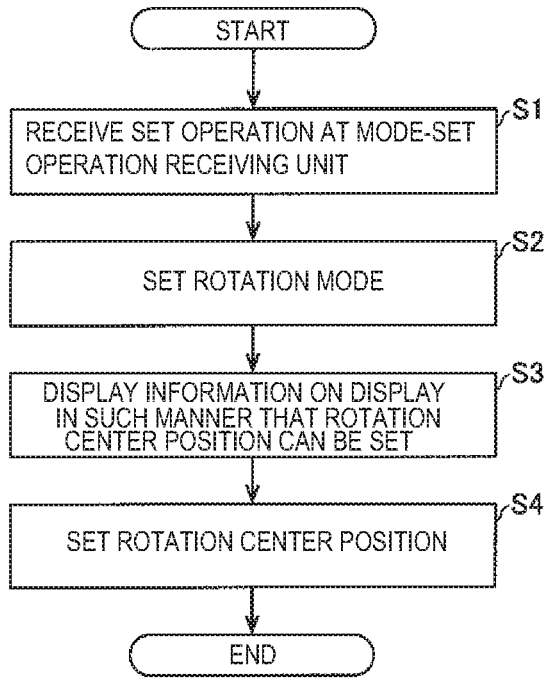
FIG. 15 is a flowchart illustrating a rotation-center-position setting process by a robotic operating table according to a first embodiment.

As illustrated in FIG. 15, first in step S1, the mode-set operation receiving unit 46 (56) receives a set operation to set the rotation mode from a medical person (user).

Then in step S2, the rotation mode selected from the yaw mode, the pitch mode, and the roll mode is set.

Then in step S3, the operation controller 41 (51) performs control that displays information on the display 42 (52) and the display 400 in such a manner that the rotation center position C can be set to one of the positions predefined for the rotation mode selected from the yaw mode, the pitch mode, and the roll mode.

Then in step S4, the position selected from the predefined positions based on an operation input by the medical person (user) is set as the rotation center position C.

(Rotation Process)

Next, a rotation process by the robotic operating table 100 in this embodiment is explained with reference to a flowchart in FIG. 16.

Figure 16:
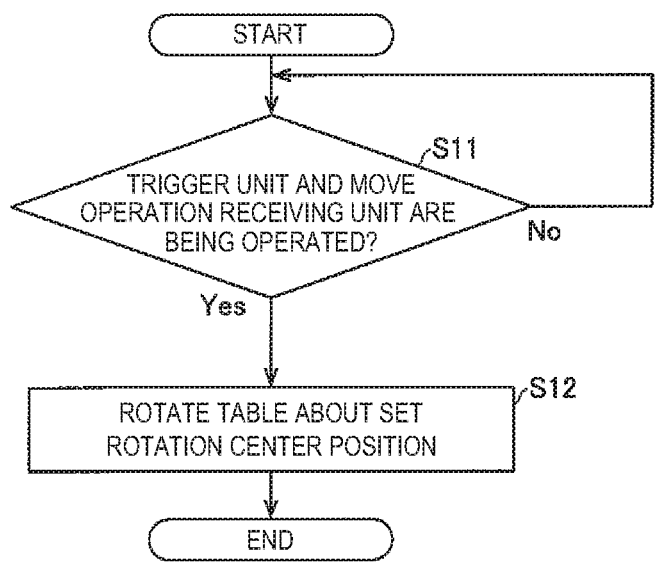
FIG. 16 is a flowchart illustrating a rotation process by a robotic operating table according to a first embodiment.

As illustrated in FIG. 16, first in step S11, it is determined whether or not the trigger unit 44 (54) and the move operation receiving unit 43 (53) of the operation device 4 (5) are being operated simultaneously.

The process of step S11 is repeated if it is determined in step S11 that the trigger unit 44 (54) and the move operation receiving unit 43 (53) are not being operated simultaneously.

If the trigger unit 44 (54) is not being operated in step S11, the motors 25 in the joints of the robotic arm 2 (horizontal joints 221 to 223 and vertical joints 231 to 233) are in the de-energized state and the electromagnetic brakes 27 are therefore braking the motors 25 in the joints, so that the table 1 does not rotate. Also, if the trigger unit 44 (54) is being operated but the move operation receiving unit 43 (53) is not being operated in step S11, the move operation receiving unit 43 (53) is not receiving any move operation from a medical person (user). The motors 25 are therefore not driven, so that the table 1 does not rotate. In other words, the table 1 is rotated about the set rotation center position C only while the trigger unit 44 (54) and the move operation receiving unit 43 (53) are operated simultaneously.

On the other hand, if it is determined in step S11 that the trigger unit 44 (54) and the move operation receiving unit 43 (53) are being operated simultaneously, the process proceeds to step S12.

Then in step S12, the controller 3 controls the motion of the robotic arm 2 to rotate the table 1 about the rotation center position C set in the rotation-center-position setting process.

(Advantageous Effects of First Embodiment)

A first embodiment can offer the following advantageous effects.

In a first embodiment, as explained above, when the mode-set operation receiving unit 46 (56) receives a set operation to set the rotation mode, the operation controller 41 (51) performs control that displays information for setting the rotation center position C to one of predefined positions on the display 42 (52). Moreover, when the move operation receiving unit 43 (53) receives a move operation with the rotation center position C set, the controller 3 controls the motion of the robotic arm 2 to rotate the table 1 about the set rotation center position C. In this way, in the case of rotating the table 1, the rotation center position C of the table 1 can be changed. As a result, the table 1 can be rotated about a specific body part of the patient 10. For example, the table 1 can be rotated about a body part on which a surgical operation or imaging is to be performed. Also, the rotation center position C can be easily changed since the rotation center position C is only required to be selected from predefined positions. Also, the robotic arm 2 is provided, which includes one end supported on the base 21 and the opposite end supporting the table 1. In this way, the table 1 can be moved by the robotic arm 2 with a large freedom of movement. Hence, the table 1, on which to place the patient 10, can have a large range and freedom of movement. As a result of these, the table 1, on which to place the patient 10, can have a large range and freedom of movement and also the rotation center position C of the table 1 can be changed. Also, since the table 1, on which to place the patient 10, can have a large range and freedom of movement, the table 1 can be moved to various positions (patient receiving position, anesthetization position, surgical operation position, imaging position, and so on) desired by medical persons such as surgeons, assistants, nurses, and medical technicians. In addition, it is possible to prevent a situation where the range of movement of the table 1 is small such that sufficient space cannot be left around the positions at which the medical persons stand. Accordingly, surgery can be performed more easily.

Also, in a first embodiment, as explained above, when the mode-set operation receiving unit 46 (56) receives a set operation to set the rotation mode, the operation controller 41 (51) performs control that displays graphic information representing the table 1 on the display 42 (52) in such a manner that the rotation center position C can be set to one of predefined positions. In this way, the rotation center position C can be changed to a desired position in a simple and intuitive manner based on the graphic information representing the table 1.

Also, in a first embodiment, as explained above, when the rotation center position C is set, the operation controller 41 (51) performs control that displays information indicating the mode name of the set rotation mode and the set rotation center position C on the display 42 (52). In this way, it is possible to easily figure out in which rotation mode and about which rotation center position C the table 1 is to be rotated.

Also, in a first embodiment, as explained above, the rotation mode includes: the yaw mode, in which the table 1 is rotated in a horizontal plane about an axis extending in the vertical direction; the pitch mode, in which the table 1 is rotated about an axis extending in parallel to the transverse direction of the table 1; and the roll mode, in which the table 1 is rotated about an axis extending in parallel to the longitudinal direction of the table 1. In this way, it is possible to change the rotation center position C of the table 1 in the yaw, the pitch, and the roll of the table 1.

Also, in a first embodiment, as explained above, the controller 3 performs control that causes the robotic arm 2 to move the table 1 while the move operation receiving unit 43 (53) is receiving a move operation. In this way, the table 1 is not moved (rotated) while the move operation receiving unit 43 (53) is not receiving a move operation. Hence, if even the move operation receiving unit 43 (53) operated unintentionally, the table 1 can be prevented from continuing to be moved unintentionally. Also, in the case of moving the table 1 intentionally too, the movement of the table 1 can be stopped simply by stopping operating the move operation receiving unit 43 (53). Hence, when the table 1 that is being moved is desired to be stopped from being moved, the movement of the table 1 can be stopped easily and quickly.

Also, in a first embodiment, as explained above, the move operation receiving unit 53 includes the move direction receivers 53*a*, which are provided respectively for directions in which to the table 1. Moreover, the controller 3 controls the motion of the robotic arm 2 to rotate the table 1 about the set rotation center position C while one of the move direction receivers 53*a* is operated in a state where the mode-set operation receiving unit 56 has received a set operation to set the rotation mode and the rotation mode has been set. In this way, the table 1 can be rotated about the set rotation center position C only by operating one of the move direction receivers 53*a*. Hence, the table 1 can be rotated about the set rotation center position C with a simple operation. Also, the table 1 is not rotated while none of the move direction receivers 53*a* is operated. In this way, the table 1 can be prevented from continuing to be rotated unintentionally. Also, in the case of rotating the table 1 about the set rotation center position C by operating the move direction receivers 53*a*, if the table 1 that is being rotated is desired to be stopped from being rotated, the rotation of the table 1 can be stopped easily and quickly.

Also, in a first embodiment, as explained above, the move operation receiving unit 43 includes the joystick 43*a*. Moreover, the controller 3 controls the motion of the robotic arm 2 to rotate the table 1 about the set rotation center position C while the joystick 43*a* is operated in a state where the mode-set operation receiving unit 46 has received a set operation to set the rotation mode and the rotation mode has been set. In this way, the table 1 can be rotated about the set rotation center position C only by operating the joystick 43*a*. Hence, the table 1 can be rotated about the set rotation center position C with a simple operation. Also, the table 1 is not rotated while the joystick 43*a* is not operated. In this way, the table 1 can be prevented from continuing to be rotated unintentionally. Also, in the case of rotating the table 1 about the set rotation center position C by operating the joystick 43*a*, if the table 1 that is being rotated is desired to be stopped from being rotated, the rotation of the table 1 can be stopped easily and quickly.

Also, in a first embodiment, as explained above, the operation device 4 (5) includes the trigger unit 44 (54), which enables operations on the move operation receiving unit 43 (53). Moreover, the controller 3 controls the motion of the robotic arm 2 to rotate the table 1 about the set rotation center position C while the trigger unit 44 (54) and the move operation receiving unit 43 (53) are operated in a state where the mode-set operation receiving unit 46 (56) has received a set operation to set the rotation mode and the rotation mode has been set. In this way, the table 1 is rotated only while both the trigger unit 44 (54) and the move operation receiving unit 43 (53) are operated. Hence, the table 1 can be prevented from being rotated unintentionally when the move operation receiving unit 43 (53) is operated unintentionally.

Also, in one or more embodiments, as explained above, the operation device 4 (5) includes the trigger unit 44 (54). Moreover, the robotic arm 2 includes joints (horizontal joints 221 to 223 and vertical joints 231 to 233). Further, each of the joints includes a motor 25 and a negative actuated-type electromagnetic brake 27. Furthermore, the controller 3 performs control that stops energization of the motor 25 to thereby actuate the electromagnetic brake 27 while the trigger unit 44 (54) is not operated, and energizes the motor 25 while the trigger unit 44 (54) is operated. In this way, the table 1 is not moved while the trigger unit 44 (54) is not moved. Hence, the table 1 can be prevented from being moved unintentionally when the move operation receiving unit 43 (53) is operated unintentionally.

Also, in one or more embodiments, as explained above, the one end of the robotic arm 2 is supported on the base 21 to be rotatable about an axis extending in the vertical direction. Also, the opposite end of the robotic arm 2 supports the table 1 at a position near its one end in the longitudinal direction of the table 1. Furthermore, the robotic arm 2 moves the table 1 with seven degrees of freedom. In this way, the table 1, on which to place the patient 10, can have a large range and freedom of movement as compared to cases where the robotic arm 2 moves the table 1 with six or fewer degrees of freedom. Moreover, with the robotic arm 2 moving the table 1 with seven degrees of freedom, the table 1 can be easily moved to desired positions.

Also, in one or more embodiments, as explained above, the table 1 includes the radiolucent part 11 and the support part 12, disposed on the one end side of the table 1 in the longitudinal direction of the table 1 and supporting the radiolucent part 11. Moreover, the opposite end of the robotic arm 2 supports the support part 12. In this way, it is possible to minimize the portion of the robotic arm 2 disposed around the radiolucent part 11. Hence, it is possible to leave a sufficient space to place the radiographic imaging apparatus 300 around the radiolucent part 11.

Second Embodiment

Next, a second embodiment is explained with reference to FIG. 1, FIG. 3, and FIG. 17 to FIG. 19. In this second embodiment is explained an example in which the rotation center position is set to any position unlike the above first embodiment, in which the rotation center position is set to one of predefined positions. Note that identical components to those in the above first embodiment are illustrated in the drawings with the same reference signs, and explanation thereof is omitted.

(Configuration of Robotic Operating Table)

As illustrated in FIG. 1, a robotic operating table 500 according to a second embodiment differs from the robotic operating table 100 in the above first embodiment in that the robotic operating table 500 includes a robot controller 503, an operation device 504, and an operation device 505. As illustrated in FIG. 3, the operation device 504 differs from the operation device 4 in the above first embodiment in that the operation device 504 includes an operation controller 541 and in that the operation device 504 includes a display 542. The operation device 505 differs from the operation device 5 in the above first embodiment in that the operation device 505 includes an operation controller 551 and in that the operation device 505 includes a display 552. In other words, a hybrid operation room system 201a in a second embodiment includes the robotic operating table 500 and a radiographic imaging apparatus 300.

Figure 17:
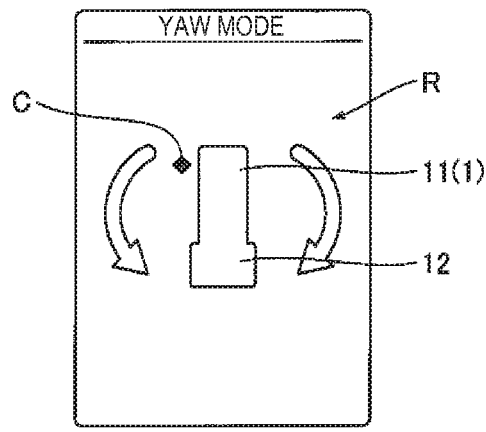
FIG. 17 is a diagram illustrating a yaw mode of a robotic operating table according to a second embodiment.
Figure 18:
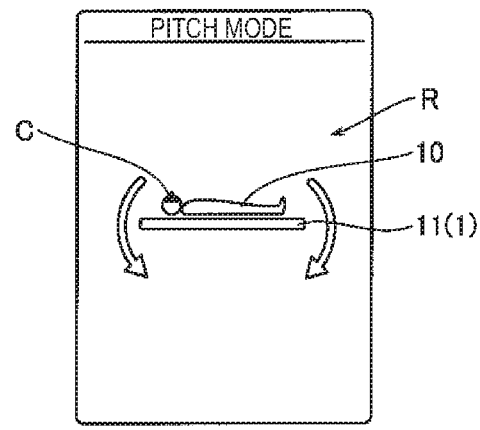
FIG. 18 is a diagram illustrating a pitch mode of a robotic operating table according to a second embodiment.
Figure 19:
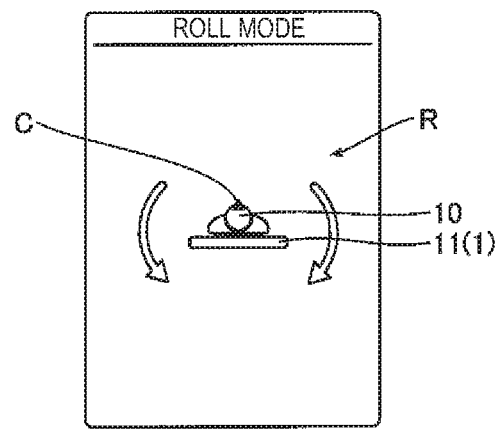
FIG. 19 is a diagram illustrating a roll mode of a robotic operating table according to a second embodiment.

As illustrated in FIG. 17 to FIG. 19, in a second embodiment, when a mode-set operation receiving unit 46 (56) receives a set operation to set the rotation mode, the operation controller 541 (551) performs control that displays information for setting a rotation center position C to any position on the display 542 (552) of the operation device 504 (505) and a display 400. Moreover, when a move operation receiving unit 43 (53) receives a move operation with the rotation center position C set, the robot controller 503 controls the motion of a robotic arm 2 to rotate a table 1 about the set rotation center position C. Each of the display 542 and the display 552 is a touchscreen-type input and display. Also, the display 400 is a touchscreen-type input and display as well.

Specifically, when the mode-set operation receiving unit 46 (56) receives a set operation to set the rotation mode, the operation controller 541 (551) performs control that displays graphic information (illustration) representing the table 1 and its surroundings on the display 542 (552) and the display 400 in such a manner that the rotation center position C can be set to any position. The operation controller 541 (551) performs control that displays a rotation-center-position setting region R covering the table 1 and its surroundings on the display 542 (552) and the display 400.

Also, when the rotation center position C is set, the operation controller 541 (551) performs control that displays information indicating the mode name of the set rotation mode and the set rotation center position C on the display 542 (552) of the operation device 504 (505) and the display 400. Also, when the rotation center position C is set, the operation controller 541 (551) performs control that displays the set rotation center position C in a visually recognizable manner on the display 542 (552) of the operation device 504 (505) and the display 400. For example, the operation controller 541 (551) performs control that displays the position set as the rotation center position C in a color different from the background color on the display 542 (552) of the operation device 504 (505) and the display 400.

As illustrated in FIG. 17, in a yaw mode, the rotation center position C can be set by selecting any position within a rotation-center-position setting region R covering the table 1 and its surroundings in a plan view (as seen from the Z direction) with a stylus. As illustrated in FIG. 18, in a pitch mode, the rotation center position C can be set by selecting any position within a rotation-center-position setting region R covering the table 1 and its surroundings in a view from the transverse direction (Y direction) with a stylus. As illustrated in FIG. 19, in a roll mode, the rotation center position C can be set by selecting any position within a rotation-center-position setting region R covering the table 1 and its surroundings in a view from the longitudinal direction (X direction) with a stylus. Note that FIG. 17 to FIG. 19 respectively illustrate images displayed on the display 542 (552) and the display 400 when the above modes are set. The rotation center position C illustrated in FIG. 17 is the position at which a tubular-element fixing tool supports a tubular element. The rotation center position C illustrated in FIG. 18 is the position of the surface of an upper portion of the head of the patient 10. The rotation center position C illustrated in FIG. 19 is the position of the surface of the upper portion of the head of the patient 10.

Also, when a set operation to set the rotation center position C is received from the user, the operation controller 541 (551) sets any position selected from within the rotation-center-position setting region R, covering the table 1 and its surroundings, as the rotation center position C.

Note that the other features of the configuration in a second embodiment are similar to those in the above first embodiment.

(Advantageous Effects of Second Embodiment)

A second embodiment can offer the following advantageous effects.

In a second embodiment, as explained above, when the mode-set operation receiving unit 46 (56) receives a set operation to set the rotation mode, the operation controller 541 (551) performs control that displays information for setting the rotation center position C to any position on the display 542 (552). Moreover, when the move operation receiving unit 43 (53) receives a move operation with the rotation center position C set, the robot controller 503 controls the motion of the robotic arm 2 to rotate the table 1 about the set rotation center position C. In this way, in the case of rotating the table 1, the rotation center position C of the table 1 can be changed. As a result, it is possible to, for example, rotate the table 1 about a specific position on the head of the patient 10. Alternatively, in a case where a fixing tool attached to the side of the table 1 is supporting a tubular element such as a respiratory tube, it is possible to rotate the table 1 without pulling the tubular element by rotating the table 1 about the position at which the fixing tool is supporting the tubular element. Moreover, since the rotation center position C can be set to any position, the rotation center position C can be freely selected and the rotation center position C can therefore be changed to a more appropriate position.

Note that the other advantageous effects of a second embodiment are similar to those of the above first embodiment.

(Modifications)

Note that one or more embodiments disclosed this time should be considered exemplary in all aspects and not limiting. The scope of the present invention is indicated by the claims rather than the explanation of the above one or more embodiments and also embraces all changes that come within the meaning and range of equivalents of the claims.

For example, although the example in which a radiographic imaging apparatus is provided in a hybrid operating room has been presented in the above, the present invention is not limited to this example. In one or more embodiments, a magnetic resonance imaging apparatus that captures a magnetic resonance image of a patient may be provided in a hybrid operating room. Also, both a radiographic imaging apparatus and a magnetic resonance imaging apparatus may be provided in a hybrid operating room.

Also, although the example in which the robotic operating table is provided in a hybrid operating room has been presented in the above, the present invention is not limited to this example. In one or more embodiments, the robotic operating table may be provided in an operating room other than a hybrid operating room.

Also, although the example in which the robotic operating table is provided with two operation devices has been presented in the above, the present invention is not limited to this example. In one or more embodiments, the robotic operating table may be provided with one operation device or provided with three or more operation devices.

Also, although the example in which the operation devices are connected to the controller so as to be capable of making wired communication with the controller has been presented in the above, the present invention is not limited to this example. For example, the operation devices may be connected to the controller so as to be capable of making wireless communication with the controller.

Also, although the example in which the rotation mode includes the yaw mode, the pitch mode, and the roll mode has been presented in the above first and second embodiments, the present invention is not limited to this example. In one or more embodiments, the rotation mode does not include all of the yaw mode, the pitch mode, and the roll mode or may include rotation modes other than the yaw mode, the pitch mode, and the roll mode.

Also, although the example in which three positions are predefined as positions that can be set as the rotation center position in each of the yaw mode, the pitch mode, and the roll mode has been presented in the above first embodiment, the present invention is not limited to this example. In one or more embodiments, two positions or four or more positions may be predefined as positions that can be set as the rotation center position.

Also, although the example in which information is displayed not only on the displays of the operation devices but also on the display provided in the operating room in such a manner that the rotation center position can be set has been presented in the above first and second embodiments, the present invention is not limited to this example. In one or more embodiments, information may not be displayed on the display provided in the operating room in such a manner that the rotation center position can be set, as long as the information is thus displayed on the displays of the operation devices.

Also, although the example in which the move direction receivers are provided for eight directions has been presented in the above, the present invention is not limited to this example. In one or more embodiments, the move direction receivers may be provided for multiple directions other than eight directions.

Also, although the example in which each register operation receiving unit includes three register operation receiving buttons has been presented in the above, the present invention is not limited to this example. In one or more embodiments, each register operation receiving unit may include one or two register operation receiving buttons or include four or more register operation receiving buttons.

Figure 20:
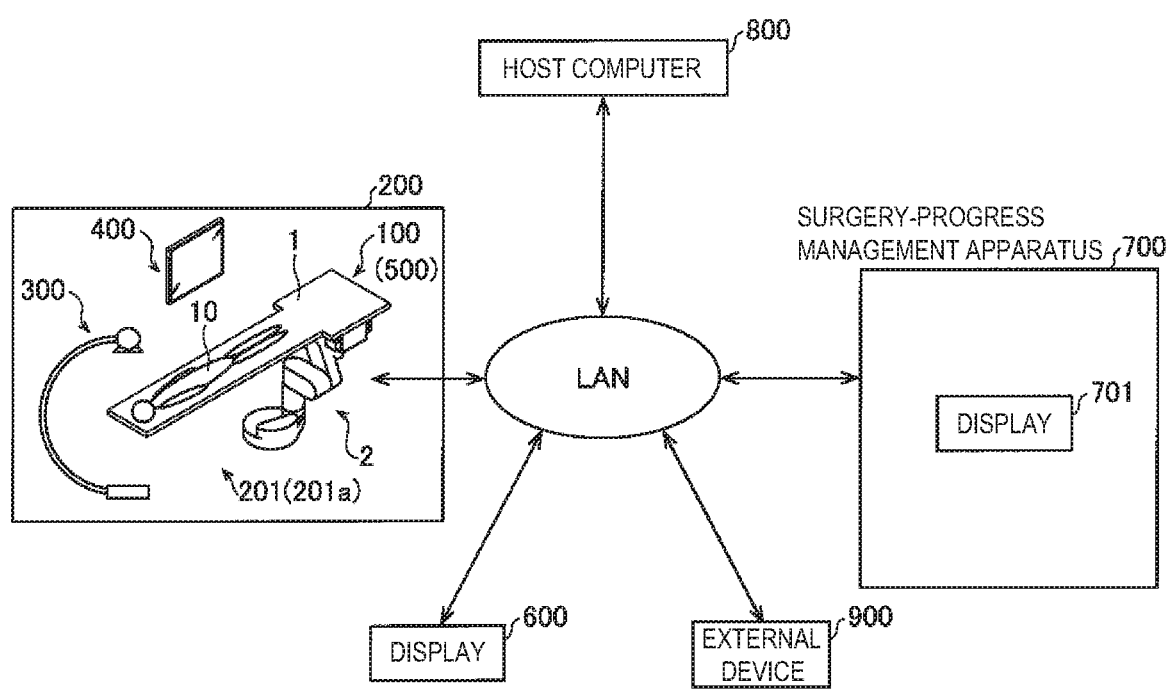
FIG. 20 is a diagram illustrating displays according to a modification of first and second embodiments.

Also, although the example in which the state of the table, the state of operation on each operation device, the operation screen, and so on are displayed on the display provided inside the operating room in addition to the display of the operation device has been presented in the above, the present invention is not limited to this example. For example, as in a modification illustrated in FIG. 20, the state of the table, the state of operation on each operation device, the operation screen, and so on may be displayed on a display provided outside the operating room. Specifically, as illustrated in FIG. 20, the state of the table and so on may be displayed on a display 600 provided outside the operating room 200 and connected to an LAN (Local Area Network) inside the hospital in which the operating room 200 is provided. The display 600 is provided in, for example, a nurses' station. Also, in a case where a surgery-progress management apparatus 700 that manages the progress of surgery is provided outside the operating room 200, the state of the table and so on may be displayed on a display 701 of the surgery-progress management apparatus 700. The display 701 of the surgery-progress management apparatus 700 is provided in, for example, a control center next to the operating room 200. Meanwhile, a host computer 800, an external device 900 such as a mobile terminal which a hospital official has, and so on may be connected to the LAN inside the hospital.

Also, although the example in which the horizontal articulated assembly includes three horizontal joints has been presented in the above, the present invention is not limited to this example. In one or more embodiments, the horizontal articulated assembly may include two horizontal joints or include four or more horizontal joints.

Also, although the example in which the vertical articulated assembly includes three vertical joints has been presented in the above, the present invention is not limited to this example. In one or more embodiments, the vertical articulated assembly may include two vertical joints or include four or more vertical joints.

Also, although the example in which the articulated robotic arm is provided with a series of three horizontal joints and a series of three vertical joints has been presented in the above, the present invention is not limited to this example. In one or more embodiments, for example, a vertical articulated robot with portions at each of which joints adjacent to each other have their rotation axes arranged perpendicular to each other, may be used as the articulated robotic arm.

Also, although the example in which the articulated robotic arm has seven degrees of freedom has been presented in the above, the present invention is not limited to this example. In one or more embodiments, the articulated robotic arm may have six or fewer degrees of freedom or have eight or more degrees of freedom. However, it is preferable for the robotic arm to have six or more degrees of freedom.

Also, although the example in which the base is buried in and fixed to the floor has been presented in the above, the present invention is not limited to this example. In one or more embodiments, the base may be fixed to the surface of the floor.

Also, although the example in which the controller is disposed inside the base has been presented in the above, the present invention is not limited to this example. In one or more embodiments, a control box with the controller housed in a casing may be provided. For example, the control box may be disposed at any position inside the operating room or the control box may be disposed in the control center next to the operating room.

Also, although the example in which the display displays the setting information for setting the rotation center position of the table has been presented in the above, the present invention is not limited to this example. In one or more embodiments, the display may display the setting information for setting the rotation axis position of the table.

The invention claimed is:

1. A robotic operating table comprising:
a table on which to place a patient; and
a robotic arm comprising a plurality of joints, and having a first end supported on a base fixed to a floor, and a second end supporting the table; and
an operation device comprising:
a mode-set operation receiving unit comprising an input device that is to be operated by an operator and receives a set operation to set a rotation mode for rotating the table;
a move operation receiving unit comprising an input device that is to be operated by the operator and receives a move operation to move the table;
a trigger unit comprising an input device that is to be operated by the operator and enables, when the trigger unit is being operated, an operation on the move operation receiving unit, and
a display; wherein
when the mode-set operation receiving unit receives the set operation to set the rotation mode, the display displays setting information for setting a rotation center position of the table, and
when the move operation receiving unit is operated to receive the move operation while the trigger unit is being operated, the robotic arm rotates the table about a rotation axis at the rotation center position.

2. The robotic operating table according to claim 1, wherein the setting information comprises information for setting one of predefined positions as the rotation center position or information for setting any position as the rotation center position.

3. The robotic operating table according to claim 1, wherein the setting information comprises graphic information representing the table and displayed in such a manner that the rotation center position is settable to one of predefined positions, or graphic information representing the table and displayed in such a manner that the rotation center position is settable to any position.

4. The robotic operating table according to claim 1, wherein when the rotation center position is set, the display displays information indicating a mode name of the rotation mode and the rotation center position.

5. The robotic operating table according to claim 1, wherein the rotation mode comprises at least one of:
a yaw mode in which the table is rotated in a horizontal plane about the rotation axis extending in a vertical direction;
a pitch mode in which the table is rotated about the rotation axis extending in parallel to a transverse direction of the table; and
a roll mode in which the table is rotated about the rotation axis extending in parallel to a longitudinal direction of the table.

6. The robotic operating table according to claim 1, wherein
the move operation receiving unit comprises move direction receivers provided respectively for directions in which to move the table, and
the robotic arm rotates the table about the rotation axis at the set rotation center position while one of the move direction receivers is operated with the rotation mode set.

7. The robotic operating table according to claim 1, wherein
the move operation receiving unit comprises a joystick, and
the robotic arm rotates the table about the rotation axis at the set rotation center position while the joystick is operated with the rotation mode set.

8. The robotic operating table according to claim 1, wherein
when the move operation receiving unit is operated to receive the move operation while the trigger unit is being operated, the robotic arm rotates, based on the received move operation, the table about the rotation axis at the set rotation center position with the rotation mode set.

9. The robotic operating table according to claim 1, wherein
each of the plurality of joints comprises a motor and an electromagnetic brake, and
while the trigger unit is not operated, the robotic arm stops energization of the motor and actuates the electromagnetic brake, and
while the trigger unit is operated, the robotic arm energizes the motor and does not actuate the electromagnetic brake.

10. The robotic operating table according to claim 1, wherein
the first end of the robotic arm is supported on the base to be rotatable about a rotation axis extending in a vertical direction,
the second end of the robotic arm supports the table at a position near an end of the table in a longitudinal direction, and
the robotic arm moves the table with at least six degrees of freedom.

11. The robotic operating table according to claim 1, wherein
the table comprises: a radiolucent part; and
a support part provided on an end of the table in a longitudinal direction of the table and supporting the radiolucent part, and
the second end of the robotic arm supports the support part.

12. A robotic operating table comprising:
a table on which to place a patient;

a robotic arm comprising a plurality of joints, and having a first end supported on a base fixed to a floor, and a second end supporting the table; and an operation device comprising:
- a mode-set operation receiving unit comprising an input device that is to be operated by an operator and receives a set operation to set a rotation mode for rotating the table;
- a move operation receiving unit comprising an input device that is to be operated by the operator and receives a move operation to move the table;
- a trigger unit comprising an input device that is to be operated by the operator and enables, when the trigger unit is being operated, an operation on the move operation receiving unit, and
- a display; wherein when the mode-set operation receiving unit receives the set operation to set the rotation mode, the display displays setting information for setting a rotation axis position of the table, and when the move operation receiving unit is operated to receive the move operation while the trigger unit is being operated, the robotic arm rotates the table about a rotation axis at the set rotation axis position.

13. The robotic operating table according to claim 12, wherein the setting information comprises graphic information representing the table and displayed in such a manner that the rotation axis position is settable to one of predefined positions, or graphic information representing the table and displayed in such a manner that the rotation axis position is settable to any position.

14. The robotic operating table according to claim 12, wherein
the robotic arm rotates the table about the rotation axis at the set rotation axis position while the trigger unit and the move operation receiving unit are operated with the rotation mode set.

15. The robotic operating table according to claim 12, wherein
each of the plurality of joints comprises a motor and an electromagnetic brake, and
the robotic arm, while the trigger unit is not operated, stops energization of the motor and actuates the electromagnetic brake, and
the robotic arm, while the trigger unit is operated, energizes the motor and does not actuate the electromagnetic brake.

16. The robotic operating table according to claim 12, wherein
the first end of the robotic arm is supported on the base to be rotatable about a rotation axis extending in a vertical direction,
the second end of the robotic arm supports the table at a position near an end of the table in a longitudinal direction, and
the robotic arm moves the table with at least six degrees of freedom.

17. An operation device with which a user operates a robotic operating table comprising a table on which to place a patient, comprising:
- a mode-set operation receiving unit comprising an input device that is to be operated by an operator and receives a set operation to set a rotation mode for rotating the table;
- a move operation receiving unit comprising an input device that is to be operated by the operator and receives a move operation to move the table;
- a trigger unit comprising an input device that is to be operated by the operator and enables, when the trigger unit is being operated, an operation on the move operation receiving unit, and
- a display, wherein the robotic operating table comprises:
- the table; and
- a robotic arm comprising a plurality of joints, and having a first end supported on a base fixed to a floor, and a second end supporting the table, and when the move operation receiving unit is operated to receive the move operation while the trigger unit is being operated, the operation device causes the robotic arm to rotate, based on the received move operation, the table about a rotation axis under the set rotation mode.

18. The operation device according to claim 17, wherein
when the mode-set operation receiving unit receives the set operation to set the rotation mode, the display displays setting information for setting a rotation center position of the table, and
the setting information comprises information for setting one of predefined positions as the rotation center position or information for setting any position as the rotation center position.

19. The operation device according to claim 17, wherein
when the mode-set operation receiving unit receives the set operation to set the rotation mode, the display displays setting information for setting a rotation center position of the table, and
the setting information comprises graphic information representing the table and displayed in such a manner that the rotation center position is settable to one of predefined positions, or graphic information representing the table and displayed in such a manner that the rotation center position is settable to any position.

20. A hybrid operation system comprising:
a robotic operating table; and
at least one of a radiographic imaging apparatus configured to capture a radiographic projection image of a patient and a magnetic resonance imaging apparatus configured to capture a magnetic resonance image of the patient,
wherein the robotic operating table comprises:
- a table on which to place the patient;
- a robotic arm comprising a plurality of joints, and having a first end supported on a base fixed to a floor, and a second end supporting the table; and
- an operation device comprising
- a mode-set operation receiving unit comprising an input device that is to be operated by an operator and receives a set operation to set a rotation mode for rotating the table,
- a move operation receiving unit comprising an input device that is to be operated the operator and receives a move operation to move the table,
- a trigger unit comprising an input device that is to be operated by the operator and enables, when the trigger unit is being operated, an operation on the move operation receiving unit, and
- a display, wherein when the mode-set operation receiving unit receives the set operation to set the rotation mode, the display displays setting information for setting a rotation center position of the table, and when the move operation receiving unit is operated to receive the move operation while the trigger unit is being operated, the robotic arm rotates the table about a rotation axis at the rotation center position.

* * * * *